(12) United States Patent
Caruthers et al.

(10) Patent No.: US 10,414,790 B2
(45) Date of Patent: Sep. 17, 2019

(54) EXOCYCLIC NITROGEN ATOM PROTECTED NUCLEOSIDE AND METHOD FOR PRODUCING AND USING THE SAME

(71) Applicants: THE REGENTS OF THE UNIVERSITY OF COLORADO, A BODY CORPORATE, Denver, CO (US); Marvin H. Caruthers, Boulder, CO (US); Subhadeep Roy, Boulder, CO (US)

(72) Inventors: Marvin H. Caruthers, Boulder, CO (US); Subhadeep Roy, Boulder, CO (US)

(73) Assignee: The Regents of the University of Colorado, Denver, CO (US)

( * ) Notice: Subject to any disclaimer, the term of this patent is extended or adjusted under 35 U.S.C. 154(b) by 570 days.

(21) Appl. No.: 14/419,033

(22) PCT Filed: Aug. 3, 2013

(86) PCT No.: PCT/US2013/053525
§ 371 (c)(1),
(2) Date: Feb. 2, 2015

(87) PCT Pub. No.: WO2014/022839
PCT Pub. Date: Feb. 6, 2014

(65) Prior Publication Data
US 2015/0225442 A1    Aug. 13, 2015

Related U.S. Application Data

(60) Provisional application No. 61/679,168, filed on Aug. 3, 2012.

(51) Int. Cl.
| | | |
|---|---|---|
| *C07H 23/00* | (2006.01) |
| *C07H 19/073* | (2006.01) |
| *C07H 19/173* | (2006.01) |
| *C07H 21/04* | (2006.01) |
| *C12N 15/11* | (2006.01) |

(52) U.S. Cl.
CPC ........... *C07H 23/00* (2013.01); *C07H 19/073* (2013.01); *C07H 19/173* (2013.01); *C07H 21/04* (2013.01); *C12N 15/11* (2013.01); *Y02P 20/55* (2015.11)

(58) Field of Classification Search
CPC .... C07H 19/073; C07H 19/173; C07H 23/00; C07H 21/04; C12N 15/11; Y02P 20/55
See application file for complete search history.

*Primary Examiner* — Lawrence E Crane
(74) *Attorney, Agent, or Firm* — Don D. Cha; HDC IP Law, LLP

(57) ABSTRACT

The present invention provides nucleosides an exocyclic amine-protected nucleoside of the formula: A-B where A is a 5'-protected ribose, 5'-protected-2-deoxyribose, 5'-protected-3'-phosphoramidite ribose, or 5'-protected-3'-phosphoramidite-2-deoxyribose moiety; and B is a nucleobase having an exocyclic amine group that is protected with di-tert-butylisobutylsilyl ("BIBS") protecting group. Use of BIBS protecting group provides an exocyclic amine-protected nucleoside that is stable to a wide variety of reaction conditions associated with oligonucleotide synthesis. The present invention also provides, oligonucleotides comprising the same, and methods for producing the same.

13 Claims, 2 Drawing Sheets
Specification includes a Sequence Listing.

Scheme 1. i. Et₃N, DMAP (0.2 equiv) and 1,4-dioxane. ii. 1.0 M NH₃/MeOH; 4h. iii. 1.2 equiv DMTr-Cl, Pyridine; 4-5 hrs.

Scheme 2. i. Et₃N, (0.2 equiv) DMAP and 1,4-dioxane. ii. 1.0 M NH₃/MeOH; 4h. iii. 1.2 equiv DMTr-Cl, Pyridine; 4-5 hrs.

3, B = C^BIBS
6, B = A^BIBS
10, B = G^BIBS, BIBS

11, B = C^BIBS
12, B = A^BIBS
13, B = G^BIBS, BIBS

Scheme 3. Synthesis of BIBS protected phosphoramidites.

Scheme 4. Synthesis cycle for preparation of bpDNA oligomers.

EXOCYCLIC NITROGEN ATOM PROTECTED NUCLEOSIDE AND METHOD FOR PRODUCING AND USING THE SAME

CROSS-REFERENCE TO RELATED APPLICATIONS

This application is U.S. National Stage Application under 35 U.S.C. § 371 of PCT Patent Application No. PCT/US13/53525, filed Aug. 3, 30213, which claims the priority benefit of U.S. Provisional Application No. 61/679,168, filed Aug. 3, 2012, all of which are incorporated herein by reference in their entirety.

FIELD OF THE INVENTION

The present invention relates to nucleosides comprising a sterically hindered silyl protecting group on the exocyclic nitrogen atom of the nucleobase, oligonucleotides comprising the same, and methods for producing the same. In particular, the silyl protecting group is a sufficiently sterically hindered such that it is stable to a typical oligonucleotide synthesis procedures.

BACKGROUND OF THE INVENTION

The solid phase synthesis of DNA oligomers requires the orthogonal protection of the 5' hydroxyl and exocyclic amines on cytosine, adenine and guanine.[i,ii] Most commonly, the 5' hydroxyl group is protected as the acid labile dimethoxytrityl ether that is removed every synthetic cycle in order to expose the hydroxyl for coupling. The amines on the other hand are protected as amides that are stable to all the reagents of the synthetic cycle and are removed at the end of the synthesis using basic conditions. However the requirements for synthesis of RNA and DNA analogs containing base sensitive modifications have led to the development of alternate protection strategies. For instance Scaringe et al[iii] have used a trimethoxytrityl protection of nucleobases along with silyl protection of 5' hydroxyl group. A different approach has resulted in the design of amide based protecting groups that are removable under very mild basic conditions or using nucleophiles.[iv] Nevertheless each of these methods has certain limitations. The trimethoxytrityl (TMTr or TMT) approach is clearly unsuited for use with 5'-dimethoxytrityl (DMT or DMTr) protection, which remains the most convenient protection group for the 5' hydroxyl moiety. At the same time the use of amides removable under mild conditions is based on faster deprotection of the exocyclic amines in presence of base labile modifications. This approach is not generalizable in practice as the time for deprotection is dependent on the composition of the bases and the length of the oligonucleotide. Many of these groups such as phenoxyacetyl,[v,vi] allyloxycarbonyl[vii] and 2,2'-bis(2-nitrophenyl)ethoxy-carbonyl[viii] are also prone to side reactions such as transamidations during the capping step. Finally all amide based protecting groups are unsuitable for the synthesis of borane containing oligonucleotide analogs where the borane reagents convert amines irreversibly to alkyl and aryl amines.

Accordingly, there is a continuing need for a protecting group on exocyclic amines in nucleobases that can be selectively removed under a relatively mild condition.

SUMMARY OF THE INVENTION

Some aspects of the invention provide an exocyclic amine-protected nucleoside, oligonucleotides comprising the same, and methods for producing the same. In one particular embodiment, the exocyclic amine-protected nucleoside is of the formula:

A-B where
A is a 5'-protected ribose, 5'-protected-2-deoxyribose, 5'-protected-3'-phosphoramidite ribose, or 5'-protected-3'-phosphoramidite-2-deoxyribose moiety;
B is a nucleobase having an exocyclic amine group that is protected with a silyl protecting group, wherein said silyl protecting group is stable to reaction conditions associated with oligonucleotide synthesis.

In some embodiments, the nucleobase is selected from the group consisting of cytosine, adenine, guanine, 2,6-diaminopurine, and 5-methylcytosine. It should be appreciated, however, that the scope of the invention is not limited to these nucleobases. In general, the scope of the invention includes any nucleobases (synthetic or otherwise) having at least one exocyclic amine group.

In other embodiments, the silyl protecting group is stable to a borane reagent. A typical borane reagent condition is disclosed in Table 3 below.

Still in other embodiments, the silyl protecting group is stable to a strongly basic condition, e.g., pH of at least 8, typically pH of at least 9, often pH of at least 10 and often pH of at least 12.

In one particular embodiment, the silyl protecting group is of the formula:

—SiR$^1$R$^2$R$^3$ where each of R$^1$, R$^2$, and R$^3$ is independently selected from the group consisting of alkyl, aryl, cycloalkyl, heteroalkyl, heteroaryl, or heterocycloalkyl each of which is optionally substituted; or two of R$^1$, R$^2$, and R$^3$ together form cycloalkyl, aryl, heteroalkyl, or heterocycloalkyl, provided at least two of R$^1$, R$^2$, and R$^3$ is sterically hindered or two of R$^1$, R$^2$, and R$^3$ together form sterically hindered cycloalkyl or sterically hindered aryl. It should be appreciated that one skilled in the art can readily determine whether a particular combination of R$^1$, R$^2$, and R$^3$ is sufficiently sterically hindered by simply performing stable to reaction conditions associated with olignonucleotide synthesis, e.g., any one of the coupling, capping, acid deprotection and oxidation reaction conditions listed in Table 3 below. Suitably sterically hindered silyl protecting groups include, but are not limited to, bis-tert-butylisobutylsilyl ("BIBS"), tri-tert-butylsilyl, alkyl-9-silylbicyclo[3.3.1]nonane or a moiety of the formula:

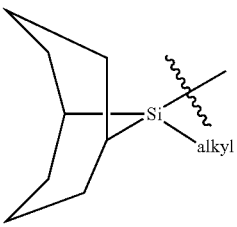

tri-isobutylsilyl, diphenyl-tert-butylsilyl, phenyl-iso-butyl-tert-butylsilyl, diphenyl-isobutylsilyl, and other sterically hindered silyl groups.

Still in other embodiments, each of R$^1$, R$^2$, and R$^3$ is independently selected from the group consisting of methyl, ethyl, n-propyl, tert-butyl, neo-pentyl, isobutyl, and isopropyl; or two of $R^1$, $R^2$, and $R^3$ together with the silyl atom to which they are attached to form 9-silylbicyclo[3.3.1]nonane.

Yet in other embodiments, the 5'-protecting group comprises an acid labile hydroxyl protecting group or a base labile hydroxyl protecting group. Suitable 5'-hydroxyl protecting groups are well known to one skilled in the art. Exemplary 5'-hydroxyl protecting groups are disclose in *Protective Groups in Organic Synthesis*, 3rd edition, T.W. Greene and P.G.M. Wuts, John Wiley & Sons, New York, 1999, and Smith and March, *Advanced Organic Chemistry*, 5$^{th}$ ed., John Wiley & Sons, New York, N.Y., 2001, which are incorporated herein by reference in their entirety. Exemplary acid or base labile hydroxyl protecting groups include, but are not limited to, dimethoxytrityl, trimethoxytrityl, monomethoxytrityl, trityl, fluorenylmethyloxy, 9-phenylxanthen-9-yl, alkylcarbonate, arylcarbonate, and other sterically blocking (i.e., sterically hindered) protecting groups.

Another aspect of the invention provides an oligonucleotide comprising a nucleobase having an exocyclic amine group that is protected with a silyl protecting group, wherein said silyl protecting group is stable to reaction conditions associated with oligonucleotide synthesis.

In some embodiments, said oligonucleotide comprises a boranephosphonate nucleotide (i.e., boranophosphonate or an oligonucleotide comprising an internucleotide linkage in which one or more oxygen atom of the phosphonate backbone is replaced with a borane group.

Yet in other embodiments, said oligonucleotide comprises at least fifteen (15) nucleotides. In other instances, said oligonucleotide comprises at least twenty (20) nucleotides.

Suitable silyl protecting groups are disclosed throughout this disclosure and include those described above.

Yet another aspect of the invention provides a method for producing an exocyclic amine-protected nucleoside of the formula A'-B. Such a method typically comprises contacting a nucleoside of the formula A'-B' with a silyl compound of the formula X—SiR$^1$R$^2$R$^3$ under conditions sufficient to produce said exocyclic amine-protected nucleoside. In this method, A' is a 5'-protected ribose or 5'-protected-2-deoxyribose moiety; B is a nucleobase having an exocyclic amine group that is protected with a silyl protecting group, wherein said silyl protecting group is stable to reaction conditions associated with oligonucleotide synthesis; B' is a nucleobase comprising an exocyclic amine group; X is a leaving group, such as (but not limited to) halide, triflate, nitro, tosylate, or sulfonate; and $R^1$, $R^2$, and $R^3$ together with silicon atom to which they are attached to forms a silyl protecting group that is stable to reaction conditions associated with oligonucleotide synthesis.

In one particular embodiment, each of $R^1$, $R^2$, and $R^3$ is independently selected from the group consisting of alkyl, aryl, cycloalkyl, heteroalkyl, heteroaryl, or heterocycloalkyl each of which is optionally substituted; or two of $R^1$, $R^2$, and $R^3$ together form cycloalkyl, aryl, heteroalkyl, or heterocycloalkyl, provided at least two of $R^1$, $R^2$, and $R^3$ is sterically hindered or two of $R^1$, $R^2$, and $R^3$ together form sterically hindered cycloalkyl or sterically hindered aryl.

Yet in other embodiments, B' is selected from the group consisting of cytosine, adenine, guanine, 2,6-diaminopurine, 5-methylcytosine, and other nucleoside bases or derivatives thereof having an exocyclic amine group known to one skilled in the art.

In some embodiments, such method further comprises the steps of contacting said exocyclic amine-protected nucleoside of the formula A'-B with a phosphitylating agent under conditions sufficient to produce a phosphoramidite compound of the formula A"-B, where A' and B are those defined above; and A" is 5'-protected-3'-phosphoramidite ribose or 5'-protected-3'-phosphoramidite-2-deoxyribose moiety.

Yet in other embodiments, the phosphitylating agent is selected from the group consisting of O-methyl-N,N-diisopropyl bisphosphoramidite, methyl N,N,N',N'-tetraisopropylphosphorodiamidite, 2-cyanoethyl N,N,N',N'-tetraisopropylphosphordiamidite, 2,2,2-trichloroethyl N,N,N',N'-tetraisopropylphosphordiamidite, dimethylcyanoethyl N,N,N',N'-tetraisopropylphosphorodiamidite, benzyl N,N,N',N'-tetraisopropylphosphorodiamidite, O-cyanoethylphosphoramidite, O-(optionally substituted benzyl) phosphoramidite, O-1,1-dimethylcyanoethylphosphoramidite, and a combination thereof. However, it should be appreciated that the scope of the invention is not limited to these phosphitylating agents. In general, any phosphitylating agents known to one skilled in the art can be used in methods of the invention.

It should be noted that each of $R^1$, $R^2$, and $R^3$ can be optionally substituted. Suitable optional substituents include nitro, acetyl, methoxy and other alkoxy groups. In some embodiments, two of $R^1$, $R^2$, and $R^3$ together form cycloalkyl, aryl, heteroalkyl, or heterocycloalkyl, each of which is optionally substituted. At least two of $R^1$, $R^2$, and $R^3$ is sterically hindered or two of $R^1$, $R^2$, and $R^3$ together form sterically hindered cycloalkyl or sterically hindered aryl.

DETAILED DESCRIPTION OF THE INVENTION

Figure 1:
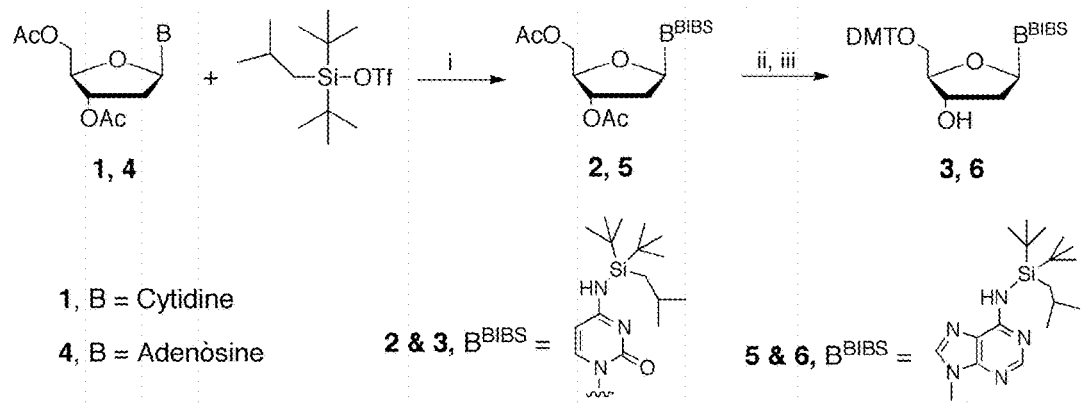
FIG. 1 is a reaction scheme for producing exocyclic amine-silyl protected 2-deoxycytidine and 2-deoxyadenosine.

"Alkyl" refers to a saturated linear monovalent hydrocarbon moiety of one to twenty, typically one to twelve, and often one to eight carbon atoms or a saturated branched monovalent hydrocarbon moiety of three to one to twenty, typically three to twelve, and often three to eight carbon atoms. Exemplary alkyl group include, but are not limited to, methyl, ethyl, n-propyl, 2-propyl, tert-butyl, pentyl, isobutyl, neo-pentyl, and the like.

"Aryl" refers to a monovalent mono-, bi- or tricyclic aromatic hydrocarbon moiety of 6 to 15 ring atoms.

"Cycloalkyl" refers to a non-aromatic, typically saturated, monovalent mono-, bi- or tricyclic hydrocarbon moiety of three to twenty, typically three to fifteen, and often three to twelve ring carbons.

"Heteroalkyl" means a branched or unbranched, acyclic saturated alkyl moiety as defined above but containing one or more heteroatoms (e.g., N, O, P, S) in place of a carbon atom in the chain.

"Heterocycloalkyl" means a non-aromatic mono-, bi-, or tricyclic moiety of three to twenty, typically three to fifteen, and often three to twelve ring atoms in which one or more ring atoms are heteroatoms selected from N, O, or $S(O)_n$ (where n is an integer from 0 to 2), the remaining ring atoms being C, where one or two C atoms can optionally be a carbonyl group.

The term "stable to reaction conditions associated with oligonucleotide synthesis" means that under a typical solid-phase or liquid-phase synthesis of oligonucleotides, at least 80%, typically at least 90%, often at least 95% and most often at least 98% of the silyl protecting group remains in tact. Typical reaction conditions associated with oligonucleotide synthesis are well known to one skilled in the art. Some exemplary reaction conditions associated with oligonucleotide synthesis can be found throughout this disclosure as well as in the references cited herein and includes one or more of the following reactions: coupling, capping, acid deprotection and oxidation. For exemplary reaction conditions for coupling (or condensation), capping, acid deprotection, and oxidation, see Table 3 below. In general, the exocyclic-amine protecting silyl group can withstand these reaction conditions such that at least 80%, typically at least 90%, often at least 95% and most often at least 98% of the silyl protecting group remains in tact.

In general, the term "stable to reaction conditions" means that the silyl protecting group remains attached to the exocyclic amine group under the reaction conditions such that at least 80%, typically at least 90%, often at least 95% and most often at least 98% of the silyl protecting group remains in tact.

Protection of Exocyclic Amines for Oligonucleotide Synthesis.

Some aspects of the invention provide a nucleoside comprising a silyl-protecting group on the exocyclic nitrogen atom (e.g., amine) and a method for producing and using the same. Silyl based protecting groups have been extensively used for protection of reactive oxygen atoms and alkyne functionalities.[ix] However, they have found very limited use for amine protection due to high degree of acid lability of the N—Si bond particularly under aqueous conditions.[x] They are also known to be unstable to oxidizing agents.

Surprisingly and unexpectedly, the present inventors have found that N-protected nucleobases comprising a sterically hindered silyl group [such as bis-tertbutylisobutylsilyl (BIBS)[xi]] are stable to a wide variety of conditions of DNA synthesis (e.g., coupling, capping, acid deprotection and oxidation) as well as strongly basic conditions and borane reagents. Moreover, it was found that these sterically hindered silyl protecting groups can be removed with mild fluoride treatment (e.g., at neutral pH). In fact, the present inventors have successfully synthesized N—BIBS-5'-DMT-2'-deoxynucleosidephosphoramidites and used these to synthesize DNA oligomers in high yields. As an example of the utility of this protection strategy in cases where amide based protection is not feasible the present inventor have successfully prepared boranophosphonate DNA (bpDNA) oligomers of lengths twice as long as previously reported.

The unique chemical properties of BIBS and other sterically hindered silyl protecting groups make them a very versatile protecting group that can be used with other combinations of both base and acid labile protecting groups. Silyl protecting groups disclosed herein are well suited for synthesis of DNA, RNA or other oligonucleotides containing base sensitive modifications or functional groups, especially in a solid phase synthesis where fluoride labile linkers attached to a solid support are used. N-silyl-protected phosphoramidites can also be used in conjunction with standard amide protected phosphoramidites which allows selective unmasking of specific nucleobases for derivatization on the solid support. As used herein, the terms "N-silyl protected" and "N-silyl protected nucleobase" refer a nucleobase that includes an exocyclic nitrogen atom (e.g., amine) that is protected with a silyl protecting group of the present invention.

Boranephosphonate DNA

Replacement of one of the non-bridging oxygen atoms in the phosphate backbone leads to a hydrolytically stable DNA analog known as boranephosphonate DNA (bpDNA).[xii] Since their first synthesis, there has been considerable interest in these molecules due to their ability to mimic DNA in several biochemical processes. In addition, the present inventors have recently discovered that these molecules are able to reduce metal ions such as $AuCl_4^-$, $PtCl_4^{2-}$ and $Ag^+$ to produce metallic nanoparticles, thereby making them highly useful in construction of DNA based metallic nanostructures. However, to date a lack of high yielding chemical methods for these analogs has greatly reduced usefulness of these compounds.

It is well recognized by one skilled in the art that previously reported methods for producing bpDNA oligomers are not applicable for a solid phase synthesis for producing a useful length of oligonucleotides in construction of oligonucleotide based metallic nanostructures. For example, previous attempts at synthesis of mixed base bpDNA oligomers using unprotected bases suggested that 10-mers could be prepared with yields of 20-30%.[xiii] Subsequently an alternative method featuring mono-nucleotide borane phosphonates and a phosphotriester strategy, has been used to prepare borane phosphonate oligomers having all four bases and up to 12 nucleotides in length but with relatively low stepwise coupling yields.[xiv] For both of these synthetic methods the low yields make them unsuitable for preparing longer oligomers. More recently the present inventors have discovered a strategy using a fluoride labile 5'-O-[benzhydroxybis(trimethylsilyloxy)]silyl (BzH) protecting group in combination with N-trimethoxytrityl protection of the nucleobases.[xv] While this method has been successfully used for synthesis of 10-14 nucleotide long oligomers in good yields, synthesis of longer (~21-mer) oligonucleotides has proven difficult. Without being bound by any theory, it is believed that the most likely reason is the degradation of the trialkylphosphite-borane backbone, present in the growing chain, to a small extend under the basic conditions (pH 9.6) used for the fluoride deprotection of the 5' BzH. It is believed that this degradation leads to the accumulation of failed sequences in the synthesis of oligomers longer than 20 nucleotides.

Some aspects of the present invention provide a sterically hindered silyl group, e.g., bis-tertbutylisobutylsilyl (BIBS), for protection of exocyclic nitrogen atom groups (e.g., amines) during oligonucleotide synthesis. Using such a highly sterically hindered silyl protecting group on an exocyclic nitrogen atom (e.g., amine), the present inventors have successfully synthesized DNA and bpDNA oligomers that are at least 15, typically at least 20, and often at least 24 nucleotides in length.

Synthesis of N-di-tertbutylisobutyl Protected Phosphoramidites

As shown in FIG. 1, the 5'- and 3'-hydroxyl groups on the deoxynucleosides were first protected as acetyl esters.[xvi] The silylation of the exocyclic amines was carried out using variations of the procedure reported by Liang et al.[11] 5',3'-di-O-acetyl-2'-deoxycytidine (1) was found to react readily at room temperature with 1.3 equivalents of bis-tertbutylisopropylsilyl triflate (BIBS-OTf) in the presence of triethylamine and N,N-dimethylaminopyridine (DMAP) as the catalyst. The reaction was complete in 2 hours and the product was obtained in good yield (67%). In contrast, the reaction with 5',3'-di-O-acetyl-2'-deoxyadenine (4) was much slower. Upon heating the reaction mixture at 60° C. for 3 days in presence of 3.0 equivalents of BIBS-OTf, the product was obtained in 25% yield. The use of a greater amount of BIBS-OTf (5 equiv.) or stronger bases (N,N-diisopropylethylamine or DBU) did not improve the yields significantly.

Figure 2:
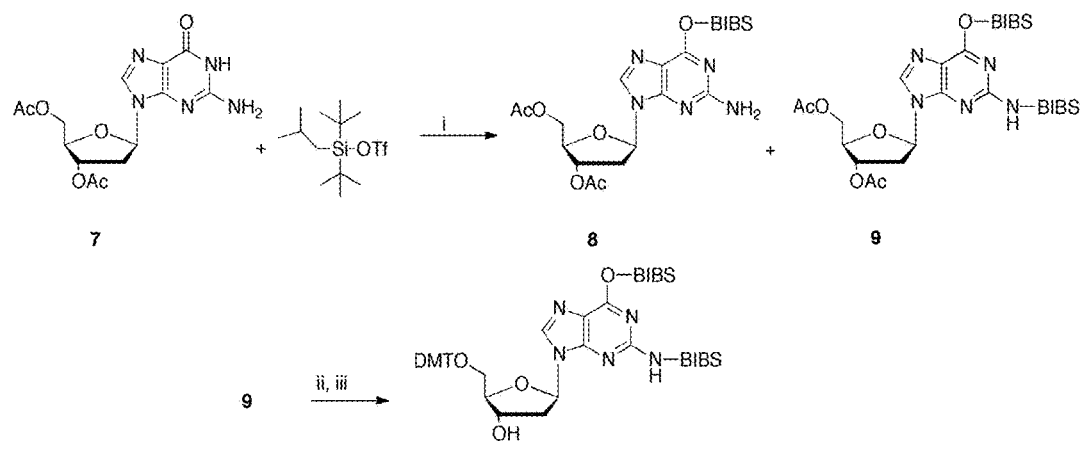
FIG. 2 is a reaction scheme for producing exocyclic amine-silyl protected 2-guanosine.

The silylation reaction with 5',3'-di-O-acetyl-2'-deoxyguanosine (7) on the other hand led to unexpected observations (FIG. 2). When the reaction of 7 was carried out with 1.2 equivalents of BIBS-OTf the major product isolated contained a single BIBS group attached to the nucleoside as evidenced by ESI-MS and $^1$H NMR. However this compound displayed poor solubility and aggregation in solvents such as dichloromethane and ethyl acetate, which is typical of $N^2$-unprotected guanosine derivatives. Further the absorbance of this compound was shifted form 260 nm to 285 nm, a well known characteristic of $O^6$-guanine derivatives. The additional absorbance band at 250 nm for 8 and 9 was also observed due to the presence of BIBS group. Without being bound by any theory, it is believed that under these conditions tautomerization followed by the reaction at $O^6$-proceeds quicker than at the $N^2$-position, leading to the formation of 8.

The reaction was repeated using a five-fold excess of BIBS-OTf to obtain the bis-silylated compound (9) as the major product in 74% yield. It was also found that the $O^6$-BIBS group of 9 was particularly labile towards acidic conditions and decomposed to monosilylated $N^2$-BIBS-5', 3'-di-O-acetyl-2'deoxyguanosine. While $O^6$-protection is not essential for the solid phase synthesis of DNA and bpDNA, the presence of two silyl groups made chromatographic purification of these derivatives particularly convenient. Thus care was taken to eliminate any acidic conditions such that both silyl groups were preserved.

Figure 3:
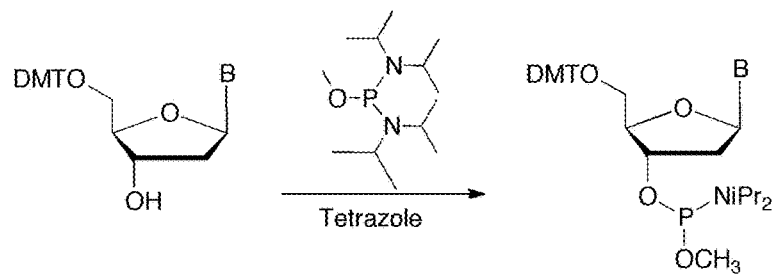
FIG. 3 is a reaction scheme for the synthesis of BIBS protected phosphoramidites.

The 5'- and 3'-acetyl groups on 2, 5 and 9 were removed by stirring in 1.0 M ammonia in methanol for 4 hrs. After evaporation of the reaction mixture under reduced pressure, the residue was dried under vacuum and reacted with dimethoxytrityl chloride in pyridine to obtain the 5'-DMT derivatives 3, 6 and 10. The 3'-OH was phosphitylated using O-methyl-N,N-diisopropyl bisphosphoramidite along with tetrazole as the activator to yield phosphoramidites 11, 12, and 13 in good yields (85-95%; FIG. 3).

Synthesis of DNA Oligomers Using N-Silyl Protected Phosphoramidites

The stability of the BIBS protected phosphoramidites towards the conditions of solid phase oligonucleotide synthesis was first tested by preparing a d($T_8$CT) oligomer. This sequence was chosen as it exposed the $N^4$-BIBS protected deoxycytidine to several rounds of the solid phase synthetic cycle. At the same time, the presence of only one base where modifications or side reactions might occur made it easier to analyze the results. At this stage, standard reagents for DNA synthesis (see Examples section) were used. O-methyl protection group of the phosphates was removed using 1.0 M disodium-2-carbamoyl-2-cyanoethylene-1,1-dithiolate in DMF followed by desilylation of the nucleobases using HF.Et$_3$N in dimethylformamide, adjusted to pH 7 with Et$_3$N. The oligonucleotide was cleaved from the solid support in 37% ammonia solution. HPLC analysis of the crude product showed that a single peak was the major product with no detectable failure sequences. However, a small shoulder with a longer retention time was also observed in the chromatogram. MALDI-TOF analysis of the crude product revealed higher molecular weight peaks that were consistent with extra 2'-deoxythymidine residues. This appeared to indicate that a small fraction of the silyl group was being lost during the solid phase synthetic cycle which allowed coupling at the $N^4$-position on the cytidine. Incorporation of a P-transfer wash following each coupling step eliminated these extra base adducts. A possibility that phosphitylation of the amine could occur in spite of the presence of the BIBS group was eliminated by synthesizing a d(CT) dimer and exposing it twenty times to the coupling mixture containing 5'-DMT-3'-O-methyl-2'-deoxythymidine-N,N-diisopropyl-phosphoramidite and ethylthiotetrazole prior to removal of the silyl group and cleavage from the solid support. The d(CT) dimer was the only product obtained.

Under acidic conditions silyl protected amines can be hydrolyzed due to protonation of the nitrogen atom that activates it towards nucleophilic attack. Thus, a test was conducted to determine whether small amounts of water present in the commercial grade deprotection mixture (3% trichloroacetic acid (TCA) in CH$_2$Cl$_2$) could be responsible for removal of the BIBS group. Exclusion of water by stirring the commercial TCA solution over P$_2$O$_5$ to remove any possible water present led to a substantially identical result as described above. In contrast, when a different acid, such as p-toluenesulfonic acid (PTSA) or trifluoroacetic acid (TFA) was used for DMT removal, the extra base adducts were not observed.

It is believed that these differences were due to the binding interactions of TCA with the growing oligomer chain. For example, Paul and Royappa[xvii] have previously reported a strong binding of TCA with CPG bound DNA oligomers that resulted in a high local concentration of the acid. The amount of TCA bound to the chain was also found to increase monotonically with increasing chain length. Thus, without being bound by any theory, it is believed that the elevated amount of local acid present, especially as the chain grown in length, may protonate the amine in spite of the bulky BIBS group that may then undergo attack by any adventitious water that is either present in the deprotection mixture or left over on the solid support from solvents used in a previous step of the solid phase synthesis.

Paul and Royappa also found that strength of the binding interaction was dependent on the nature of the acid and dichloroacetic acid showed weaker binding than TCA. It is believed that PTSA and TFA do not interact strongly with the growing chain oligonucleotides, thereby preventing hydrolysis of BIBS. The use of PTSA for synthesis of oligomers containing adenosine or guanosine showed extensive depurination. However, a solution of 0.5% TFA in HCCl$_3$ for removal of the 5'-DMT was used for subsequent syntheses.

Using these slightly modified conditions, d(T$_8$AT) and d(T$_8$GT) were also prepared to test the synthons 12 and 13 for synthesis of deoxyoligonucleotides. The desired products were obtained in high yields with no detectable side products by HPLC and MALDI-TOF analysis.

One of the most rigorous tests of the suitability of any synthon for solid phase synthesis is to repeatedly join them to a 2'-deoxythymidine attached to a solid support. This process amplifies any problems that arise during chain elongation and cleavage. Synthesis of d(C$_9$T) and d(A$_9$T) yielded one major product that was confirmed by MALDI-TOF to be the correct product. Consecutive coupling of 2'-deoxyguanosine led to low yields. In addition, 2'-deoxyguanosine homopolymers aggregate rendering their analysis by HPLC problematic. Thus a d(GT)$_5$ was prepared to test 13. The HPLC profile of this oligomer also contained only one major peak. However, in comparison to d(C$_9$T) and d(A$_9$T), a greater number of failure sequences were observed. In none of the cases any peaks with molecular weights higher than the expected mass were found during MALDI-TOF analysis (Table 1).

TABLE 1

DNA oligomers synthesized using BIBS protected phosphoramidites.

| Sequences | Mass (theor) | Mass (Obs.) |
|---|---|---|
| 5'-TTTTTTTTCT-3' (SEQ ID NO: 1) | 2963.4 | 2964.96 |
| 5'-TTTTTTTTAT-3' (SEQ ID NO: 2) | 2987.5 | 2987.63 |
| 5'-TTTTTTTTGT-3' (SEQ ID NO: 3) | 3003.7 | 3008.5 |
| 5'-CCCCCCCCCT-3' (SEQ ID NO: 4) | 2843.5 | 2846.84 |
| 5'-AAAAAAAAAT-3' (SEQ ID NO: 5) | 3059.6 | 3061.17 |
| 5'-GTGTGTGTGT-3' (SEQ ID NO: 6) | 3103.3 | 3108.07 |
| 5'-GCATGCATGCAT-3' (SEQ ID NO: 7) | 3643.6 | 3643.92 |

To test these three synthons simultaneously, d(TACG)$_3$ oligomers were prepared. The HPLC profile showed a single major peak. In addition, a small peak that eluted at a longer time than the main peak was observed. Characterization of the crude product by MALDI-TOF, however, did not reveal any products with molecular weights higher than the calculated mass. These results show that with only slight modification of the conditions of solid phase DNA synthesis, nucleotides comprising a nucleobase with a sterically hindered silyl protecting group on the exocyclic nitrogen atom (e.g., with BIBS) are useful in preparation of oligonucleotides such as deoxyribonucleic acid oligomers. It should be appreciated that the term "oligonucleotide" refers to a deoxyribonucleotide or ribonucleotide polymer and unless otherwise limited, encompasses known analogs of natural nucleotides. Examples of such analogs include, but are not limited to, phosphorothioates, phosphoramidates, methyl phosphonates, chiral-methyl phosphonates, 2-O-methyl ribonucleotides, and peptide-nucleic acids (PNAs).

Figure 4:
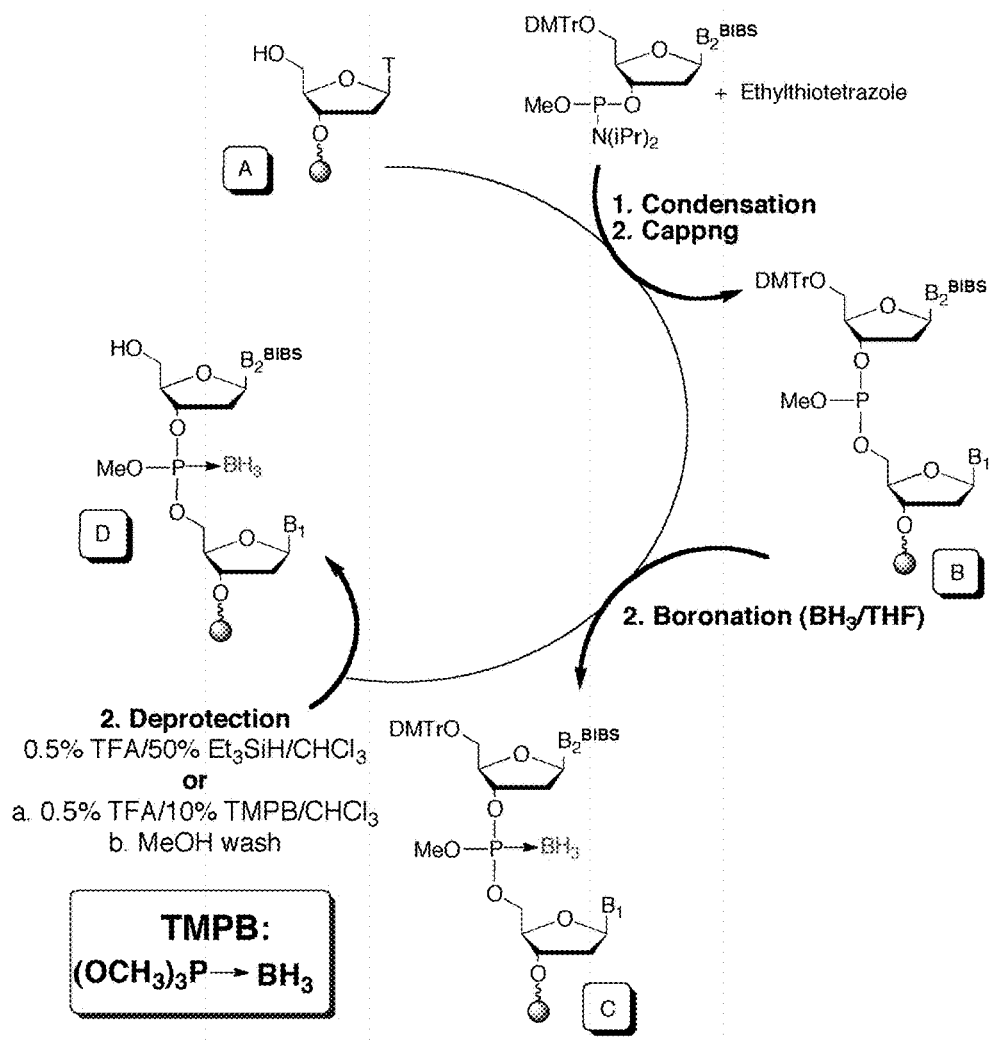
FIG. 4 is a reaction scheme for the synthesis cycle for preparation of bpDNA oligomers.

Synthesis of bpDNA Oligomers: Trimethylphosphite-borane as a trityl cation Quencher For synthesis of bpDNA, the oxidation step is replaced by a boronation step that yields a trialkylphosphite-borane linkage (Structure C, FIG. 4). However, the trityl cations generated during the subsequent acid deprotection step reacts with these linkages present in the growing bpDNA chain and cause degradation.[xvii,xix] Previously, triethylsilane has been used as an additive to the deptoection mixture to quench trityl cations in the synthesis of 10-12 mer bpDNA oligomers.[vii,xx] To test whether these conditions were suitable for synthesis of longer bpDNA oligomers, 21-mer bpDNA oligothymidines were prepared. Two different synthetic methods using commercially available 5'-DMT-3'-O-β-cyanoethyl-2'deoxythymidine-N,N-diisopropylphosphoramitide and 5'-DMT-3'-O-methyl-2'-deoxythymidine-N,N-diisopropylphosphoramidite were carried out. Both of the product mixtures revealed significant amounts of failure products when analyzed using 20% denaturing gel electrophoresis. It is believed that the trityl cation reacts with the oligomer backbone to some degree even in the presence of a large excess of triethylsilane. Based on these results, it is believed that an analog of the trialkylphosphite-borane linkages that is present in the solid support bound bpDNA could be a more efficient quencher of trityl cations.

Trimethylphosphite-borane (TMPB) (FIG. 4) was synthesized by reaction of trimethylphosphite with a slight excess of dimethylsulfide borane complex in dichloromethane. The solvents and excess Me$_2$S.BH$_3$ were removed under reduced pressure to yield TMPB as a clear oil. The synthesis of a 21-mer boranephosphonate linked deoxyoligothymidine was then repeated using a deprotection mixture that contained 10% (v/v) TMPB in a solution of 0.5% TFA in CHCl$_3$. 5'-DMT-3'-O-methyl-2'-deoxythymidine-N,N-diisopropylphosphoramidite was used in this synthesis (Table 2, bpODN2). Polyacrylamide gel electrophoresis showed that the failure products were effectively suppressed. The reaction of trimethylphosphite-borane with the dimethoxytrityl cation produced insoluble borates, which can interfere with subsequent coupling reaction. Incorporation of a methanol wash following the deprotection step was used to remove these precipitates.

TABLE 2

Sequences of bpDNA oligomers synthesized. No subscript between nucleobases refers to boranephosphonate linkages. In other cases p = phosphate and b = boranephosphonate.

| Sequence name. | Sequences | Mass (theor.) | Mass (Obs.) |
|---|---|---|---|
| bpODN1 | 5'-TTTTTTTTTT-3' (SEQ ID NO: 8) | 2951.7 | 2956.23 |
| bpODN2 | 5'-TTTTTTTTTTTTTTTTTTTTT-3' (SEQ ID NO: 9) | 6279.61 | 6249.34 |
| bpODN3 | 5'-T$_p$T$_p$T$_p$T$_p$T$_p$T$_p$T$_p$T$_p$T$_p$T$_p$-T$_b$T$_b$T$_b$T$_b$T$_b$T$_b$T$_b$T$_b$T$_b$T$_b$T-3' (SEQ ID NO: 10) | 6309.31 | 6281.31 |
| bpODN4 | 5'-TTTTTTTCT-3' (SEQ ID NO: 11) | 2936.78 | 2942.93 |

TABLE 2-continued

Sequences of bpDNA oligomers synthesized. No subscript between nucleobases refers to boranephosphonate linkages. In other cases p = phosphate and b = boranephosphonate.

| Sequence name. | Sequences | Mass (theor.) | Mass (Obs.) |
|---|---|---|---|
| bpODN5 | 5'-TTTTTTTTAT-3' (SEQ ID NO: 12) | 2960.79 | 2963.59 |
| bpODN6 | 5'-TTTTTTTTGT-3' (SEQ ID NO: 13) | 2976.78 | 2977.95 |
| bpODN7 | 5'-CAGTGACCGCATCGGACAGCAGCT-3' (SEQ ID NO: 14) | 7291.95 | 7282.26 |
| bpODN8 | 5'-$C_pA_pG_pT_bG_pA_pC_pC_bG_pC_pA_pT_bC_pG_p$-$G_pA_bC_pA_pG_pC_bA_pG_pC_pT$-3' (SEQ ID NO: 15) | 7344.40 | 7326.4 |

Synthesis of bpDNA Oligomers Using BIBS Protected Phosphoramidite

Fully boronated bpd($T_8$CT), bpd($T_8$AT) and bpd($T_8$GT) oligomers (Table 2, bpODN4, bpODN5 and bpODN6, respectively) were prepared to test synthons 11, 12 and 13 for synthesis of bpDNA. The deprotection mixture contained 10% TMPB in a 0.5% solution of TFA in CHCl$_3$. The oxidation step was replaced by boronation using a solution of 0.05 M BH$_3$.THF complex in anhydrous THF. Denaturing gel electrophoresis showed the formation of a single band and all oligomers were confirmed by MALDI-TOF to be the correct product (Table 2). Two 24-mer boranephosphonate oligomers containing all four nucleobases were prepared: one was fully boronated at every phosphate linkage (bpODN7) whereas the other contained a mixture of boranephosphonate and phosphate linkages (bpODN8). For the second oligomer, the phosphate linkages were produced by oxidation with a 1.0 M tert-butyl peroxide (tBuOOH) solution in anhydrous CH$_2$Cl$_2$. A single band was observed in polyacrylamide gel electrophoresis for the fully boronated oligomer indicating that the product was formed in high yields. The mixed phosphate-boranephosphonate oligomer produced a more diffuse band in the gel possibly indicating that a small degree of decomposition of the boranephosphonate occurs during the peroxide oxidation steps. Both oligomers were also analyzed using MALDI-TOF MS and $^{31}$P NMR.

Conclusion

Using a sterically hindered silyl group (e.g., bis-tertbutylisobutylsilyl) as an exocyclic nitrogen atom protecting group of a nucleobase can be used to prepare phosphoramidites. These nucleotides comprising a sterically hindered silyl protecting group can be used in synthesis of DNA and bpDNA oligomers. The nucleotides disclosed herein can be used in solution phase and/or solid phase based oligonucleotide synthesis. The nucleotides of the invention are particularly useful in automated solid phase synthesis of oligonucleotides. Silyl protection of amines in general is not commonly used in organic synthesis due to their acid lability. Solid phase synthesis of DNA requires strong acids to remove the dimethoxytrityl protection of the 5'-hydroxyl. As a result, silyl protecting groups have not been used as viable protecting groups for the exocyclic amines which require a protecting group that is stable throughout the synthetic cycles but can be readily be removed when desired, e.g., at the end of the oligonucleotide synthesis.

It was discovered by the present inventors that the BIBS protecting group and other silyl protecting groups of the invention possess suitable stereochemical properties that make them stable to oligonucleotide synthesis conditions. Silyl protecting groups of the invention are stable also to strong basic conditions. However, silyl protecting groups of the invention can be removed under mild, neutral pH conditions using fluoride ions. These properties make silyl protecting groups of the invention versatile protecting group that is useful in the synthesis of a wide variety of oligonucleotides. Especially in cases where amide protected exocyclic amines and/or their removal under basic conditions are problematic. For instance, in conjunction with fluoride labile silyl or linkers used for solid support attachment, synthons similar to those described herein can also be used in applications for completely base-free oligonucleotide (e.g., DNA and RNA) synthesis.

On particular application where current conventional amide protecting groups are unsuitable is in the synthesis of borane containing oligonucleotide (e.g., oligodeoxyribonucleotide) analogs. The synthesis of bpDNA using 5'-DMT protected phosphoramidites requires solving at least two problems. First, the protection of exocyclic amines requires stability of this group towards reduction by borane reagents. Silyl protecting groups of the invention avoid this problem as the experiments showed they were stable to the conditions of boronation.

Second, in a solid phase synthesis, the reactivity of trityl cations that are produced during DMT removal need to be attenuated as they react with the solid support bound trialkylphosphite-borane chain. Previously, triethylsilane has been used in the acidic deprotection mixture as a scavenger or DMT reactivity attenuator. The present inventors have discovered that for the preparation of longer bpDNA oligomers, Et$_3$SiH was not an efficient attenuator of the trityl cation reactivity. When trimethylphosphite-borane was added to the deprotection mixture, it effectively suppressed degradation reactions. Thus, using a combination of a sterically hindered silyl protecting group (e.g., BIBS) to protect an exocyclic nitrogen atom of phosphoarmidites and TMPB as a trityl scavenger resulted in a successful synthesis of mixed base bpDNA oligomers of a relatively large number of nucleotides (e.g., 24 nucleotides or more) in high yields and purity. Such a long chain bpDNA oligonucleotides are useful in a wide variety of applications including, but not limited to, studying binding and biochemical properties, and their use as therapeutics.

Trityl quenchers have been investigated in the past in DNA and RNA synthesis for preventing the recombination of the trityl cation and the hydroxyl group as this leads to shorter length products. This problem is particularly acute for large scale DNA synthesis. Thus, discovery by the present inventors of a new highly efficient class of quenchers eliminates these problems.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

General

All chemicals were purchased from Sigma-Aldrich unless otherwise noted. All standard reagents for use in automated DNA synthesis as well as 5'-dimethoxytrityl-2'-deoxythymidine-3'-[(methyl)-(N,N-diisopropyl)]-phosphoramidite were purchased from Glen research. All starting 2'-deoxynuceosides were purchased from ChemGenes Corporation. Di-terbutylisobutylsilyl triflate was purchased from Gelest Inc. Trimethylphosphite was obtained from Strem Chemicals. Triethylamine was dried by refluxing over $CaH_2$ and distilled fresh prior to use. Deuterated solvents were purchased from Cambridge Isotopes.

NMR Experiments were carried out on a Bruker Avance-III 300 spectrometer at 300 MHz. Chemical shifts are given in ppm with positive shifts downfield: all $^1H$ and $^{13}C$ chemical shifts were referenced relative to internal residual protons from a lock solvent.

HPLC analyses were carried out on an Agilent 1100 series system using a C-18 reverse phase column. A mobile phase of 100% 50 mM Triethylammonium bicarbonate buffer (pH 8.5) to 50% acetonitrile over 40 minutes was used.

Polyacrylamide gel electrophoresis was conducted at 100 V using 20% polyacrylamide gels (7.5 cm length) containing 7 M urea. The oligos were dissolved in a Tris-EDTA buffer containing 7.0 M urea and heated to 95° C. followed by cooling to room temperature prior to loading on the gel. The gels were stained using SYBR GOLD nucleic acid stain.

Synthesis: $N^2$-di-tert-butylisobutylsilyl-3', 5'-di-O-acetyl 2' deoxycytidine (2)

3',5'-Di-O-acetyl-2'-deoxycytidine (1) (933 mg, 3 mmol) was dried under vacuum overnight in a round bottom flask. N,N-Dimethylaminopyridine (DMAP) (73.2 mg, 0.6 mmol) was added to the flask, which was then repeatedly flushed with Argon. Subsequently, 10 mL of 1,4-dioxane and freshly distilled triethylamine (0.61 g, 6.0 mmol) was added via syringe. Lastly di-terbutylisobutylsilyltriflate (1.4 g, 3.9 mmol) was added to the flask via syringe and the mixture was stirred at 50° C. for 2 h when TLC (9:1; $CHCl_3$:MeOH) indicated all starting material had disappeared. The reaction was stopped by diluting in 75 mL of ethyl acetate and pouring it into 75 mL of saturated $NaHCO_3$. The organic layer was extracted twice with 75 mL of saturated $NaHCO_3$ and once with 50 mL brine. The ethyl acetate layer was then dried over sodium sulfate and evaporated to dryness. The mixture was purified by flash chromatography on a silica gel column. The silica gel slurry was initially made in a mixture of 47.5:47.5:5 mixture of ethyl acetate:hexanes:triethylamine and poured into the column followed by washing it with two column volumes of ethyl acetate-hexanes (1:1) mixture of before loading the product mixture. The product was eluted using a gradient of 1:1 ethyl acetate-hexanes to 7:3 ethyl acetate-hexanes to yield 1.03 g of a white foam (67% yield). $^1H$ NMR ($CDCl_3$): δ 7.54 (1H, d, $C_6$); 6.25 (1H, t, 1'); 5.78 (1H, bs, NH); 5.17 (1H, d, $C_5$); 4.30-4.32 (2H, m, 5'); 4.26 (1H, m, 4'); 2.67 (1H, dd, 2'); 2.07 (3H, s, acetyl); 2.05 (3H, s, acetyl); 2.01 (1H, m, 2'); 1.07 (18H, s, BIBS); 0.94-0.97 (8H, m, BIBS). $^{13}C$ NMR ($CDCl_3$): δ 20.81, 20.86, 20.90, 20.93, 21.07, 24.79, 26.37, 28.38, 28.78, 38.72, 63.94, 74.37, 82.30, 86.59, 96.48, 139.59, 168.12, 170.34, 170.47. ESI-MS (m/z): 510.3 $(M+H)^+$, 532.2 $(M+Na)^+$.

$N^6$-di-tert-butylisobutylsilyl-3', 5'-di-O-acetyl-2'-deoxyadenosine (5)

3',5'-Di-O-acetyl 2' deoxyadenosine (4) (877 mg, 2.6 mmol) was dried overnight under vacuum in a round bottom flask. N,N-Dimethylaminopyridine (63 mg, 0.52 mmol) was added to the flask which was then fitted with an air condenser with a rubber septum. This assembly was flushed with argon followed by addition of 10 mL of 1,4-dioxane and 1.1 mL (10.4 mmol) of freshly distilled triethylamine. Di-terbutylisobutylsilyltriflate (2.7 g, 7.8 mmol) was then added via syringe and the mixture was stirred at 75° C. for two days. The reaction was stopped by diluting in 75 mL of ethyl acetate and pouring it into 75 mL of saturated $NaHCO_3$. The organic layer was extracted twice with 75 mL saturated $NaHCO_3$ and once with 50 mL brine. The ethyl acetate layer was then dried over sodium sulfate and evaporated to dryness. Subsequently the mixture was purified by flash chromatography on a silica gel column. The silica gel slurry was initially made in a mixture of 47.5:47.5:5 mixture of ethyl acetate:hexanes:triethylamine and poured into the column followed by washing it with two column volumes of 1:1 mixture of ethyl acetate-hexanes before loading the product mixture. The product was eluted using a 1:1 hexanes-ethyl acetate mixture to obtain a glassy pale yellow oil (0.35 g, 25% yield). $^1H$ NMR ($CDCl_3$): δ 8.35 (1H, s, C8); 7.94 (1H, s, C2); 6.42 (1H, t, 1'); 5.42 (1H, m, 3'); 5.34 (1H, bs, N6); 4.34-4.43 (3H, m, C4' and C5'); 2.95 (1H, pentet, C2'); 2.60 (1H, m, C2'); 2.13 (3H, s, acetyl); 2.09 (3H, s, acetyl); 1.14 (18H, s, BIBS); 1.03 (2H, m, BIBS); 0.97 (6H, d, BIBS). $^{13}C$ NMR ($CDCl_3$): 14.35, 20.95, 21.09, 21.22, 24.95, 26.60, 26.64, 27.41, 28.50, 28.98, 37.65, 63.98, 74.78, 82.61, 84.64, 138.01, 152.94, 170.46, 170.58. ESI-MS: 534.3 $M+H)^+$, 556.3 $(M+Na)^+$.

$N^2$, $O^6$-bis[di-tert-butylisobutylsilyl]-3', 5'-di-O-acetyl-2' deoxyguanosine (9)

3',5'-Di-O-acetyl 2' deoxyguanosine (7) (0.527 g, 1.5 mmol) was co-evaporated thrice with anhydrous pyridine and dried overnight in a round bottom flask under vacuum to remove trace amounts of water. Subsequently, DMAP (36.6 mg, 0.3 mmol) was added to the flask which was then fitted with an air condenser with a rubber septum. This assembly was flushed repeatedly with argon and anhydrous 1,4-dioxane (5 mL), freshly distilled triethylamine (1 mL) and di-terbutylisobutylsilyltriflate (2.5 g; 7.1 mmol) was added via syringe. The reaction was then stirred at 60° C. for two days. Reaction mixture was diluted with 50 mL ethyl acetate and the organic layer was washed twice with saturated NaHCO$_3$ solution and once with brine. Organic layer was dried over Na$_2$SO$_4$, filtered and evaporated under reduced pressure. The product was purified by flash chromatography. As before, the silica gel slurry was initially made in a mixture of 47.5:47.5:5 mixture of ethyl acetate:hexanes:triethylamine and poured into the column followed by washing it with two column volumes of 1:1 mixture of ethyl acetate-hexanes before loading the product mixture. The product was eluted using a hexanes-ethyl acetate (1:1) mixture to obtain a white foam (0.9 g, 80.3% yield). $^1$H NMR (CD$_2$Cl$_2$): 7.81 (1H, s, C8); 6.33 (1H, t, 1'); 5.28 (1H, m, 3'); 4.51, (1H, bs, N2); 4.31 (3H, m, 4' and 5'); 2.43-2.58 (2H, m, 2'); 2.10 (3H, s, acetyl); 2.09 (3H, s, acetyl), 1.90 (2H, septet, BIBS), 1.14 (18H, s, BIBS), 1.12 (18H, s, BIBS), 0.92-1.02, (16H, m, BIBS). $^{13}$CNMR (CD$_2$Cl$_2$): δ 21.22, 21.28, 21.33, 21.35, 21.39, 21.98, 22.49, 25.29, 25.45, 26.87, 26.91, 28.65, 28.69, 28.74, 28.76, 29.26, 29.29, 39.45, 53.64, 54.00, 54.36, 64.43, 75.08, 82.68, 84.54, 117.67, 136.44, 154.78, 159.94, 161.35, 170.72, 170.88. ESI-MS: 748.5 (M+H)$^+$, 771.5 (M+Na)$^+$.

Removal of Acetyl Groups

5',3'-Di-O-acetyl-N-BIBS protected 2'-deoxynucleosides (2, 5 and 8) were dissolved in methanol followed by addition of an equal volume of 2.0 M ammonia in methanol and stirred for 4-5 hours. TLC (7:3 ethyl acetate-hexanes) showed complete disappearance of starting material and formation of a single product, at which point the mixture was evaporated to dryness and dried overnight under vacuum. This mixture was used directly for the next step.

General Procedure for Formation of 5'-O-dimethoxytrityl ethers

The BIBS protected nucleoside was dissolved in anhydrous pyridine followed by addition of 1.2 equivalents of dimethoxytrityl chloride. For compound 10, an additional 4 equivalents of anhydrous N,N-diisopropylethylamine was added to prevent the loss of the O$^6$—BIBS groups. The mixture was stirred at room temperature for 4-5 hours and followed by thin layer chromatography. Upon completion, the mixture was diluted in ethyl acetate and extracted twice with saturated NaHCO$_3$ and once with brine. The organic layer was dried over Na$_2$SO$_4$ and evaporated to dryness. The mixture was then purified by flash chromatography on a silica gel column. In all cases the silica gel slurry was made with the starting eluant mixture containing an additional 5% triethylamine. After pouring the slurry, the column was then washed with two column volumes of the starting solvent mixture containing no triethylamine. Compounds 3 and 6 were eluted using a gradient of 1:1 ethyl acetate-hexanes to 100% ethyl acetate. Compound 10 was eluted using a gradient of 1:1 hexanes-diethyl ether to 1:9 hexanes-diethyl ether. The yields described in the following sections represent the obtained yields over two steps starting from the 5',3'-di-O-acetyl-N-BIBS protected 2'-deoxynuceosides.

N$^2$-di-tert-butylisobutylsilyl-5'-dimethoxytrityl-2' deoxycytidine (3)

85% yield. $^1$H NMR (CDCl$_3$): δ 7.91 (1H, d, C6); 7.4 (2H, m, DMT); 7.22-7.31 (7H, m, DMT); 6.82 (4H, d, DMT); 6.37 (1H, t, 1'); 5.50 (1H, d, C5); 4.53 (1H, b, 3'); 4.09 (1H, m, 4'); 3.79 (s, 6H, DMT); 3.38-3.49 (2H, qd, 5'); 3.02 (1H, bs, O3'); 2.59-2.67 (1H, m, 2'); 2.20-2.29 (1H, m, 2'); 2.00 (1H, septet, BIBS); 1.07 (18H, s, BIBS); 0.94 (6H, d, BIBS); 0.90 (2H, d, BIBS). $^{13}$C NMR (CDCl$_3$): δ 14.35, 21.03, 21.06, 21.20, 24.92, 26.45, 26.53, 28.93, 42.20. 55.36, 63.22, 71.69, 86.02, 86.34, 86.91, 96.24, 113.37, 127.14, 128.08, 128.29, 129.26, 130.23, 135.58, 135.69, 144.65, 158.73. ESI-MS: 729.4 (M+H)$^+$, 751.4 (M+Na)$^+$.

N$^6$-di-tert-butylisobutylsilyl-5'-dimethoxytrityl-2' deoxyadenosine (6)

(72% yield)$^1$H NMR (CD$_2$Cl$_3$): δ 8.24 (1H, s, C8); 7.88 (1H, s, C2); 7.41 (2H, m, DMT); 7.32 (7H, m, DMT); 6.81 (4H, d, DMT); 6.39 (1H, t, C1'); 4.66 (1H, m, C3'); 4.09 (2H, m, C4' and N6); 3.77 (6H, s, DMT); 3.36 (2H, dd, C5'); 2.83 (1H, pentet, C2'); 2.46 (1H, m, C2'); 2.23 (1H, d, O3'); 2.09 (1H, septet, BIBS); 1.14 (18H, s, BIBS); 1.04 (2H, dd, BIBS); 0.96 (6H, dd, BIBS). ESI-MS: 752.4 (M+H)$^+$, 774.4 (M+Na)$^+$.

N$^2$, O$^6$-bis[di-tert-butylisobutylsilyl]-5'-dimethoxytrityl-2' deoxyguanosine (10)

70% yield. $^1$H NMR (CDCl$_3$): 7.73 (1H, s, C8); 7.42 (2H, m, DMT); 7.21-7.33 (7H, m, DMT); 6.83 (4H, d, DMT); 6.31 (1H, t, 1'); 4.47 (2H, m, 3' and N2); 4.05 (1H, q, 4'); 3.79 (6H, s, DMT); 3.45 (1H, dd, 5'); 3.32 (1H, dd, 5'); 2.44 (2H, td, 2'); 2.16 (1H, septet, O6-BIBS); 2.03 (1H, septet, N2-BIBS); 1.92 (1H, d, O3'); 1.14 (18H, bs, O6-BIBS); 1.11 (18H, bs, N2-BIBS); 0.90-1.01 (18H, m, O6, N2-BIBS). $^{13}$C NMR (CDCl$_3$): 20.87, 21.06, 21.09, 21.66, 22.18, 24.85, 25.01, 26.64, 26.69, 26.74, 28.49, 29.05, 41.46, 55.38, 72.69, 83.79, 85.03, 86.82, 113.43, 127.12, 128.13, 128.17, 130.13, 135.70, 135.76, 136.50, 144.60, 158.74, 160.78. ESI-MS: 966.6 (M+H)$^+$.

General Method for Synthesis of Phosphoramidites

The 5'-dimethoxytrityl-N-BIBS protected nucleosides were added to a round bottom flask which was flushed with argon. Then anhydrous dichloromethane and methyl N,N,N',N'-tetraisopropylphosphorodiamidite (1.2 equivalents) were added via syringe. Subsequently, 1 equivalent of tetrazole (0.4 M in CH$_3$CN) was added dropwise to this solution over half an hour while stirring. The reaction was then stirred at room temperature for 2-3 hours more. The reaction mixture was then diluted in dichloromethane and extracted twice with saturated solution of NaHCO$_3$. The organic layer was dried over Na$_2$SO$_4$, filtered and evaporated to dryness. The products were purified by flash chromatography on a silica column. In all cases the silica gel slurry was made with the starting eluant mixture containing an additional 5% triethylamine. After pouring the slurry, the column was washed with two column volumes of the starting solvent mixture containing no triethylamine. Compounds 11 and 12 were purified using a gradient of 7:3 hexanes-ethyl acetate to 1:1 hexanes-ethyl acetate. Compound 13 was purified using a 7:3 hexanes-diethyl ether mixture.

N$^2$-Di-tert-butylisobutylsilyl-5'-dimethoxytrityl-2' deoxycytidine-3'-O-methyl-N,N-diisopropylphosphoramidite (11)

86% yield. $^{31}$P NMR (CDCl$_3$): 148.36, 149.30 (diastereomers). $^1$H NMR (CDCl$_3$): 7.93 (1H, dd, C6), 7.41 (2H, m, DMT); 7.22-7.31 (7H, m, DMT), 6.80-6.84 (4H, dd, DMT);

6.31-6.39 (1H, m, 1'); 5.42 (1H, d, C5); 4.57-4.73 (2H, m, 3', 4'); 4.13 (m, 1H; 5'); 3.79 (6H, s, DMT); 342-3.62 (3H, m, 5' and iPr); 3.22, 3.26, 3.34, 3.39 (3H, dd, O-methyl); 2.57-2.74 (1H, m, 2'); 2.20-2.30 (1H, m, 2'); 2.00 (1H, septet, BIBS); 1.13 (12H, m, iPr); 1.06 (18H, s, BIBS); 0.94 (6H, dd, BIBS); 0.89 (2H, d, BIBS). $^{13}$C NMR (CDCl$_3$): 21.00, 21.06, 21.17, 24.77, 24.93, 26.42, 26.55, 28.97, 42.97, 43.05, 43.13, 43.22, 50.51, 50.74, 55.35, 62.85, 72.56, 77.36, 86.11, 86.23, 86.83, 96.02, 113.30, 127.08, 128.02, 128.38, 130.31, 135.53, 135.69, 135.77, 144.62, 144.71, 158.70. ESI-MS (m/z): 889.5 (M+H)$^+$, 895.5 (M+Li)$^+$, 911.5 (M+Na)$^+$.

$N^6$-Di-tert-butylisobutylsilyl-5'-dimethoxytrityl-2'deoxyadenosine-3'-O-methyl-N,N-diisopropylphosphoramidite (12)

95% yield. $^{31}$P NMR (CD$_2$Cl$_2$): 149.10, 148.90 (diastereomers). $^1$H NMR (CD$_2$Cl$_2$): δ 8.24 (1H, s, C8); 7.90 (1H, d, C2); 7.41 (2H, m, DMT); 7.30 (4H, m, DMT); 7.22 (3H, m, DMT); 6.80 (4H, dd, DMT); 6.80 (1H, t, C1'); 4.72 (1H, m, C3'); 4.25 (1H, sextet, C4'); 3.77 (6H, s, DMT); 3.58 (2H, m, C5'); 3.58, 3.39, 3.36, 3.28 (3H, P—OCH$_3$); 2.86 (1H, septet, C2'); 2.56 (1H, m, C2'); 2.09 (1H, septet; BIBS); 1.17 (8H, dd, iPr); 1.14 (18H, s, BIBS); 1.11 (4H, d, iPr); 1.04 (2H, d, BIBS); 0.96 (gH, dd, BIBS). $^{13}$C NMR (CDCl$_3$): δ 20.78, 21.01, 24.33, 24.37, 24.42, 24.78, 26.18, 26.22, 28.69, 42.90, 43.00, 63.52, 63.75, 73.21, 73.38, 73.68, 73.85, 84.35, 85.51, 85.77, 86.29, 113.02, 126.70, 127.74, 128.04, 128.07, 129.99, 130.01, 130.07, 135.70, 135.78, 135.88, 135.94, 138.59, 138.62, 144.86, 144.92, 149.19, 152.34, 158.06, 158.60. ESI-MS: 913.5 (M+H)+, 935.5 (M+Na}$^+$, 951.5 (M+K)$^+$.

$N^2,O^6$-Bis[di-tert-butylisobutylsilyl]-5'-dimethoxytrityl-2' deoxyguanosine-3'-O-methyl-N,N-diisopropylphosphoramidite (13)

89% yield. $^{31}$P NMR (CDCl$_3$): 148.44, 149.31 (diastereomers). $^1$H NMR (CDCl$_3$): 7.82, 7.78 (1H, s, C8); 7.44 (2H, m, DMT); 7.17-7.45 (7H, m, DMT); 6.81 (4H, dd, DMT); 6.35 (1H, m, 1'); 4.56 (1H, m, 3'); 4.47 (1H, s, N2); 4.26 (1H, m, 4'); 3.78 (6H, s, DMT); 3.57 (2H, m, iPr); 3.39, 3.35, 3.27, 3.23 (3H, dd, P—OCH$_3$); 2.46-2.65 (1H, m, 2'); 2.36 (1H, m, 2'); 2.16 (1H, septet, O6-BIBS); 2.02 (1H, septet, N2-BIBS); 1.17 (6H, s, iPr); 1.14 (24H, broad, iPr and 06-BIBS); 1.11 (18H, d, N2-BIBS); 0.90-1.01 (18H, m, O6, N2-BIBS). 13C NMR (CD$_2$Cl$_2$): d −2.33, −2.15, −2.08, −1.50, −0.96, 1.57, 1.67, 1.70, 1.78, 1.87, 3.37, 3.52, 3.58, 5.35, 5.94, 19.82, 19.91, 19.98, 20.08, 32.19, 90.16, 103.78, 104.85, 105.10, 112.69, 112.84, 113.43, 121.55, 135.45, 136.26, 137.57. ESI-MS: 1127.7 (M+H)$^+$.

Automated DNA Synthesis

TABLE 3

Synthesis cycle for bpDNA oligomers.

| Step | Reagent/Conditions | Time |
|---|---|---|
| Detritylation | 10% TMPB + 0.5% TFA in CHCl$_3$ | Flow 35 s |
| Wash | MeOH | Flow 20 s, wait 10 s, flow 10 s. |
| Wash | Anhydrous CH$_3$CN | Flow 20 s |
| Condensation | 0.1M phosphoramidite 11, 12 (in CH$_3$CN) or 13 (in CH$_2$Cl$_2$) + Activator* (0.25M ethylthiotetrazole in CH$_3$CN). | 120 s |
| Capping | Cap A* (THF/Pyridine/Ac$_2$) + Cap B* (16% 1-methylimidazole in THF) | Flow 10 s, wait 5 s |
| Wash | Anhydrous CH$_3$CN | Flow 10 s |
| Oxidation or | 1.0M tert-butyl hydroperoxide in CH$_2$Cl$_2$ | Flow 8 s, wait 15 s |
| Boronation | 0.05M BH$_3$—THF in THF | Flow 15 s, wait 45 s |
| Wash | Anhydrous CH$_3$CN | Flow 10 s |
| Wash | Anhydrous CH$_2$Cl$_2$ | Flow 25 s |

*Standard reagents purchased from Glen research.

Deprotection was carried out in two steps. First the solid support bound oligomers was treated with a 1.0M solution of disodium-2-carbamoyl-2-cyanoethylene-1,1-dithiolate in DMF for 1 hour followed by extensive washing with DMF and methanol. Subsequently the oligomers were desilylated by overnight treatment with fluoride ions in DMF (940 μL DMF + 470 μL Et$_3$N + 630 μL Et$_3$N•(HF)$_3$). The resin was once again washed repeatedly with DMF, Millipore water and methanol and dried with argon. It was then transferred to a glass vial and suspended in 37% ammonia for 1-2 hours and the ammonia was evaporated in a SpeedVac. The cleaved oligomers were dissolved in a 10% acetonitrile-water mixture and used for further analyses.

Automated DNA synthesis was carried out using an ABI 394 Synthesizer. All syntheses were performed at a 0.2 μmol scale using a 5'-DMT-2'-deoxythymidine linked to a low volume polystyrene solid support. For DNA oligomers described here, a standard 0.2 μmole synthesis cycle was used with an increased coupling time of 120 s. Phosphoramidites (dT, 11 and 12) were dissolved in anhydrous CH$_3$CN whereas 13 was dissolved in CH$_2$Cl$_2$ to a concentration of 0.1 M. Other standard reagents used initially (Glen research) were: 1. Activator (0.25 M ethylthiotetrazole), 2. Cap A (THF/Pyridine/Ac$_2$O), 3. Cap B (16% 1-methylimidazole in THF), 3. Oxidizing Solution (0.02M I$_2$ in THF/Pyridine/H$_2$O) and 4. Deblock (3% trochloroacetic acid in CH$_2$Cl$_2$). The deblock solution was later replaced by a 0.5% solution of trifluoroacetic acid in anhydrous CHCl$_3$. For bpDNA oligomers further modifications to this cycle are described in Table 3 above.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

REFERENCES

[i]. H. G. Khorana. *Science* 1979, 203, 614.
[ii]. M. H. Caruthers. *Biochem. Soc. Trans.* 2011, 39, 575.
[iii]. S. A. Scaringe, F. E. Wincott, and M. H. Caruthers, *J Am. Chem. Soc.* 1998, 120, 11820.
[iv]. P. Virta *ARKIVOC* 2009, (iii) 54.
[v]. Zhu, Q.; Delaney, M. O.; Greenberg, M. M. *Bioorg. Med. Chem. Lett.* 2001, 11, 1105.
[vi]. Seio, K.; Negishi, T.; Negishi, K.; Sekine, M. *Lett. Org. Chem.* 2005, 2, 179.

[vii]. Spinelli, N.; Meyer, A.; Hayakawa, Y.; Imbach, J.-L.; Vasseur, J.-J. *Eur. J. Org. Chem.* 2002, 49.

[viii]. Alvarez, K.; Vasseur, J.-J.; Beltran, T.; Imbach, J.-L. *J. Org. Chem.* 1999, 64, 6319.

[ix]. (a) Wuts, P. G. M.; Greene, T. W. *Greene's Protective Groups in Organic Synthesis*, 4th ed.; Wiley-Interscience: New York, 2007. (b) Kocienski, P. Protecting Groups, 3rd ed.; Thieme: Stuttgart, 2005. (c) Nelson, T. D.; Crouch, R. D. *Synthesis* 1996, 1031

[x]. (a) Pratt, J. R.; Massey, W. D.; Pinkerton, F. H.; Thames, S. F. *J. Org. Chem.* 1975, 40, 1090. (b) Smith, A. B.; Visnick, M.; Haseltine, J. N.; Sprengeler, P. A. *Tetrahedron* 1986, 42, 2957.

[xi]. H. Liang, L. Hu, and E. J. Corey, *Org. Lett.* 2011, 13, 4120.

[xii]. (a) P. Li, Z. A. Sergueeva, M. Dobrikov and B. R. Shaw *Chem. Rev.* 2007, 107, 4746 (b) A. Sood, B. R. Shaw and B. F. Spielvogel, *J. Am. Chem. Soc.* 1990, 112, 9000 (c) J. Tomasz, B. R. Shaw, K. Porter, B. F. Spielvogel, and A. Sood *Angew. Chem. Int. Ed.* 1992, 31, 1373.

[xiii]. Sergueev, D. S.; Sergueeva, Z. A.; Shaw, B. R. *Nucleosides, Nucleotides, Nucleic Acids* 2001, 20, 789-795.

[xiv]. (a) Shimizu, M.; Wada, T.; Oka, N.; Saigo, K. *J. Org. Chem.* 2004, 69, 5261-5268. (b) M. Shimizu, K. Saigo, and T. Wada *J. Org. Chem.* 2006, 71, 4262.

[xv]. H. B. McCuen, M. S. Noe, A. B. Sierzchala, A. P. Higson, and M. H. Caruthers, *J Am. Chem Soc.* 2006, 128, 8138.

[xvi]. M. Ikejiri, M. Saijo, S. Morikawa, S. Fukushi, T. Mizutani, I. Kuraneb and T. Maruyama *Bioorg. Med. Chem. Lett.* 2008, 17, 2470.

[xvii]. C. H. Paul and A. T. Royappa. *Nucleic Acids Res.* 1996, 24, 3048

[xviii]. Sergueeva, Z. A.; Sergueev, D. S.; Shaw, B. R. *Nucleosides Nucleotides* 2001, 20, 941-945.

[xix]. A. P. Higson, A. Sierzchala, H. Brummel. Z. Zhao and M. H. Caruthers, Tetrahedron Lett. 1998, 39, 3899

[xx]. M. Shimizu, T. Wada, N. Oka, and K. Saigo. *J. Org. Chem.* 2004, 69, 5261.

---

What is claimed is:

1. An exocyclic amine-protected nucleoside of the formula:

A-B wherein
A is a 5'-protected-2'-deoxyribosyl, or 5'-protected-3'-phosphoramidityl-2'-deoxyribosyl moiety; and
B is a nucleobase having an exocyclic amine group that is protected with di-tert-butylisobutylsilyl protecting group.

2. The exocyclic amine-protected nucleoside of claim 1, wherein said nucleobase is selected from the group consisting of 2,6-diamino-9-purinyl, 9-adeninyl, 9-guaninyl, 2,6-diamino-9-purinyl, and 5-methyl-1-cytosinyl.

3. The exocyclic amine-protected nucleoside of claim 1, wherein a 5'-protecting group is selected from the group consisting of an acid labile hydroxyl protecting group and a base labile hydroxyl protecting group.

4. The exocyclic amine-protected nucleoside of claim 3, wherein said 5'-protecting group is selected from the group consisting of dimethoxytrityl, trimethoxytrityl, monomethoxytrityl, trityl, fluorenylmethyloxy, 9-phenylxanthen-9-yl, alkyl carbonate, and aryl carbonate.

5. A deoxyribonucleic acid oligonucleotide comprising a nucleobase having an exocyclic amine group that is protected with a di-tert-butylisobutylsilyl protecting group.

6. The deoxyribonucleic acid oligonucleotide of claim 5, wherein said oligonucleotide comprises a boranephosphonate nucleotide.

7. The deoxyribonucleic acid oligonucleotide of claim 5, wherein said oligonucleotide comprises at least fifteen (15) nucleotides.

8. The deoxyribonucleic acid oligonucleotide of claim 7, wherein said oligonucleotide comprises at least twenty (20) nucleotides.

9. A method for producing an exocyclic amine-protected nucleoside of the formula A'-B, said method comprising contacting a nucleoside of the formula A'-B' with a silyl compound of the formula $X\text{---}SiR^1R^2R^3$ under conditions sufficient to produce said exocyclic amine-protected nucleoside, wherein
A' is a 5'-protected-2'-deoxyribosyl moiety;
B is a nucleobase having an exocyclic amine group that is protected with a di-tert-butylisobutylsilyl protecting group;
B' is a nucleobase having an exocyclic amine group;
X is a leaving group; and
one of $R^1$, $R^2$, and $R^3$ is isobutyl and the other two are tert-butyl.

10. The method of claim 9, wherein X is a halide, triflate, nitro, tosylate, or sulfonate.

11. The method of claim 9, wherein B' is selected from the group consisting of 2,6-diamino-9-purinyl, 9-adeninyl, 9-guaninyl, 2,6-diamino-9-purinyl, and 5-methyl-1-cytosinyl.

12. The method of claim 9 further comprising the steps of contacting said exocyclic amine-protected nucleoside of the formula A'-B with a phosphitylating agent under conditions sufficient to produce a phosphoramidite compound of the formula A"-B, wherein
A' and B are those defined in claim 9; and
A" is or 5'-protected-3'-phosphoramidite-2-deoxyribosyl moiety.

13. The method of claim 12, wherein said phosphitylating agent is selected from the group consisting of O-methyl-N,N-diisopropyl bisphosphoramidite, methyl N,N,N',N'-tetraisopropylphosphorodiamidite, 2-cyanoethyl N,N,N',N'-tetraisopropylphosphordiamidite, 2,2,2-trichloroethyl N,N,N',N'-tetraisopropylphosphordiamidite, dimethylcyanoethyl N,N,N',N'-tetraisopropylphosphorodiamidite, benzyl N,N,N',N'-tetraisopropylphosphorodiamidite, O-cyanoethylphosphoramidite, O-(optionally substituted benzyl) phosphoramidite, O-1,1-dimethylcyanoethylphosphoramidite, and a combination thereof.

* * * * *

SEQUENCE LISTING

```
<160> NUMBER OF SEQ ID NOS: 15

<210> SEQ ID NO 1
<211> LENGTH: 10
<212> TYPE: DNA
<213> ORGANISM: Artificial Sequence
<220> FEATURE:
<223> OTHER INFORMATION: Oligonucleotide

<400> SEQUENCE: 1
ttttttttct                                                              10

<210> SEQ ID NO 2
<211> LENGTH: 10
<212> TYPE: DNA
<213> ORGANISM: Artificial Sequence
<220> FEATURE:
<223> OTHER INFORMATION: Oligonucleotide

<400> SEQUENCE: 2
ttttttttat                                                              10

<210> SEQ ID NO 3
<211> LENGTH: 10
<212> TYPE: DNA
<213> ORGANISM: Artificial Sequence
<220> FEATURE:
<223> OTHER INFORMATION: Oligonucleotide

<400> SEQUENCE: 3
ttttttttgt                                                              10

<210> SEQ ID NO 4
<211> LENGTH: 10
<212> TYPE: DNA
<213> ORGANISM: Artificial Sequence
<220> FEATURE:
<223> OTHER INFORMATION: Oligonucleotide

<400> SEQUENCE: 4
ccccccccct                                                              10

<210> SEQ ID NO 5
<211> LENGTH: 10
<212> TYPE: DNA
```

```
<213> ORGANISM: Artificial Sequence
<220> FEATURE:
<223> OTHER INFORMATION: Oligonucleotide

<400> SEQUENCE: 5
aaaaaaaaat                                                                   10

<210> SEQ ID NO 6
<211> LENGTH: 10
<212> TYPE: DNA
<213> ORGANISM: Artificial Sequence
<220> FEATURE:
<223> OTHER INFORMATION: Oligonucleotide

<400> SEQUENCE: 6
gtgtgtgtgt                                                                   10

<210> SEQ ID NO 7
<211> LENGTH: 12
<212> TYPE: DNA
<213> ORGANISM: Artificial Sequence
<220> FEATURE:
<223> OTHER INFORMATION: Oligonucleotide

<400> SEQUENCE: 7
gcatgcatgc at                                                                12

<210> SEQ ID NO 8
<211> LENGTH: 10
<212> TYPE: DNA
<213> ORGANISM: Artificial Sequence
<220> FEATURE:
<223> OTHER INFORMATION: Base Pair Oligonucleotide
<220> FEATURE:
<221> NAME/KEY: misc_feature
<222> LOCATION: (1)..(10)
<223> OTHER INFORMATION: Boranephosphonate linkage between nucleosides

<400> SEQUENCE: 8
tttttttttt                                                                   10

<210> SEQ ID NO 9
<211> LENGTH: 21
<212> TYPE: DNA
<213> ORGANISM: Artificial Sequence
<220> FEATURE:
<223> OTHER INFORMATION: Base Pair Oligonucleotide
<220> FEATURE:
<221> NAME/KEY: misc_feature
<222> LOCATION: (1)..(21)
<223> OTHER INFORMATION: boranephosphonate linkage between nucleosides

<400> SEQUENCE: 9
tttttttttt tttttttttt t                                                      21

<210> SEQ ID NO 10
<211> LENGTH: 21
<212> TYPE: DNA
<213> ORGANISM: Artificial Sequence
<220> FEATURE:
<223> OTHER INFORMATION: bp Oligonucleotide
<220> FEATURE:
<221> NAME/KEY: misc_feature
<222> LOCATION: (11)..(21)
<223> OTHER INFORMATION: boranephosphonate linkage between nucleosides

<400> SEQUENCE: 10
tttttttttt tttttttttt t                                                      21
```

-continued

```
<210> SEQ ID NO 11
<211> LENGTH: 9
<212> TYPE: DNA
<213> ORGANISM: Artificial Sequence
<220> FEATURE:
<223> OTHER INFORMATION: bp Oligonucleotide
<220> FEATURE:
<221> NAME/KEY: misc_feature
<222> LOCATION: (1)..(9)
<223> OTHER INFORMATION: boranephosphonate linkage between nucleosides

<400> SEQUENCE: 11 tttttttct                                                                    9

<210> SEQ ID NO 12
<211> LENGTH: 10
<212> TYPE: DNA
<213> ORGANISM: Artificial Sequence
<220> FEATURE:
<223> OTHER INFORMATION: bp Oligonucleotide
<220> FEATURE:
<221> NAME/KEY: misc_feature
<222> LOCATION: (1)..(10)
<223> OTHER INFORMATION: boranephosphonate linkage between nucleosides

<400> SEQUENCE: 12
tttttttat                                                                   10

<210> SEQ ID NO 13
<211> LENGTH: 10
<212> TYPE: DNA
<213> ORGANISM: Artificial Sequence
<220> FEATURE:
<223> OTHER INFORMATION: bp Oligonucleotide
<220> FEATURE:
<221> NAME/KEY: misc_feature
<222> LOCATION: (1)..(10)
<223> OTHER INFORMATION: boranephosphonate linkage between nucleosides

<400> SEQUENCE: 13
ttttttttgt                                                                  10

<210> SEQ ID NO 14
<211> LENGTH: 24
<212> TYPE: DNA
<213> ORGANISM: Artificial Sequence
<220> FEATURE:
<223> OTHER INFORMATION: bp Oligonucleotide
<220> FEATURE:
<221> NAME/KEY: misc_feature
<222> LOCATION: (1)..(24)
<223> OTHER INFORMATION: boranephosphonate linkage between nucleosides

<400> SEQUENCE: 14
cagtgaccgc atcggacagc agct                                                  24

<210> SEQ ID NO 15
<211> LENGTH: 24
<212> TYPE: DNA
<213> ORGANISM: Artificial Sequence
<220> FEATURE:
<223> OTHER INFORMATION: bp Oligonucleotide
<220> FEATURE:
<221> NAME/KEY: misc_feature
<222> LOCATION: (4)..(5)
<223> OTHER INFORMATION: boranephosphonate linkage between nucleosides
<220> FEATURE:
<221> NAME/KEY: misc_feature
<222> LOCATION: (8)..(9)
```

```
<223> OTHER INFORMATION: boranephosphonate linkage between nucleosides
<220> FEATURE:
<221> NAME/KEY: misc_feature
<222> LOCATION: (12)..(13)
<223> OTHER INFORMATION: boranephosphonate linkage between nucleosides
<220> FEATURE:
<221> NAME/KEY: misc_feature
<222> LOCATION: (16)..(17)
<223> OTHER INFORMATION: boranephosphonate linkage between nucleosides
<220> FEATURE:
<221> NAME/KEY: misc_feature
<222> LOCATION: (20)..(21)
<223> OTHER INFORMATION: boranephosphonate linkage between nucleosides

<400> SEQUENCE: 15
cagtgaccgc atcggacagc agct                                              24
```